(12) United States Patent
Asatourian et al.

(10) Patent No.: US 6,361,549 B1
(45) Date of Patent: Mar. 26, 2002

(54) METHOD FOR TREATING TREMORS

(76) Inventors: Anton Asatourian, 626 1/2 E. Maple St., Glendale, CA (US) 91205; Benjamin Sup Hyun, 1210 N. Cherokee Ave., #221, Los Angeles, CA (US) 90038; Gil Lipaz, 1917 Livonia Ave., Los Angeles, CA (US) 90034

( * ) Notice: Subject to any disclaimer, the term of this patent is extended or adjusted under 35 U.S.C. 154(b) by 0 days.

(21) Appl. No.: 09/562,518

(22) Filed: May 1, 2000

Related U.S. Application Data

(60) Provisional application No. 60/133,446, filed on May 13, 1999.

(51) Int. Cl.⁷ .............................................. A61B 17/00
(52) U.S. Cl. ...................................................... 606/204
(58) Field of Search ................................ 606/201, 202, 606/203, 204, 1, 192, 191

(56) References Cited

U.S. PATENT DOCUMENTS

| | | |
|---|---|---|
| 4,149,532 A | 4/1979 | Terry et al. |
| 4,237,873 A | 12/1980 | Terry et al. |
| 4,784,120 A | 11/1988 | Thomas |
| 5,063,913 A | 11/1991 | Nyi |
| 5,441,058 A | 8/1995 | Fareed |
| 5,478,306 A | 12/1995 | Stoner |
| 5,601,597 A * | 2/1997 | Arrowood et al. ........... 606/203 |
| 5,695,520 A * | 12/1997 | Bruckner et al. ........... 606/204 |
| 5,865,775 A | 2/1999 | Peoples et al. |
| 5,901,379 A | 5/1999 | Hirata |
| 6,027,521 A * | 2/2000 | Ourada ........................ 606/204 |

* cited by examiner

Primary Examiner—Kevin Truong
(74) Attorney, Agent, or Firm—Lyon & Lyon LLP

(57) ABSTRACT

A method of suppressing tremors in the extremities of human beings by applying pressure to at least one selected location on the extremity.

9 Claims, 1 Drawing Sheet

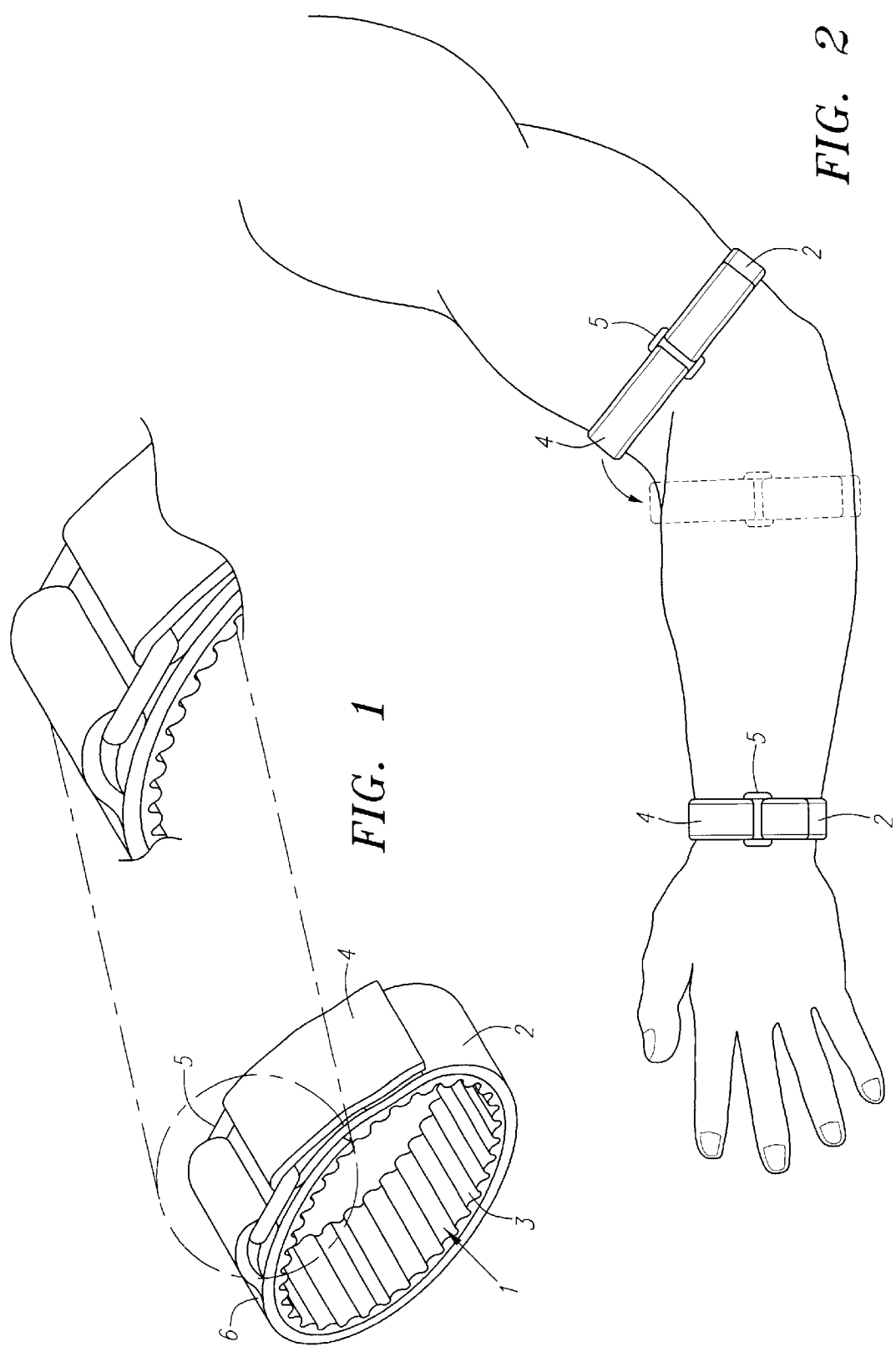

METHOD FOR TREATING TREMORS

RELATED APPLICATIONS

The present application claims priority based on Provisional Application No. 60/133,446, filed May 13, 1999.

FIELD OF THE INVENTION

The suppression of tremors in the extremities of human beings.

BACKGROUND OF THE INVENTION

The present invention relates to a method and apparatus for treating tremors in the extremities of humans. Tremors in humans are associated with several medically defined disorders. One such disorder is Essential tremor. Parkinson's disease is another such disorder. Those who suffer from such disorders experience excessive and involuntary oscillation of their limbs, which results in loss of control of attempted performance of an action or attempted maintenance of a postural position.

Present methods of treating such tremor disorders include medication such as Propranolol, Primidone, and Benzodiazepines, but these are often poorly tolerated and/or lose efficacy with prolonged treatment. A procedure known as "deep brain stimulation" has also been used with some success, but it is not effective for some patients and has the disadvantages of high expense and the risk of intracerebral hemorrhage or stroke. In addition, this procedure, which involves drilling a hole through the skull and into the brain, is subject to the difficulty that gaining access to the desired part of the brain is more difficult in some subjects that others.

Historically, deep brain stimulation has involved the creation of subcortical lesions in the thalamus and, in some cases, in the ansa lenticularis. Other tremor disorders that have been found to respond to a lesion in the thalamic area, particularly in the ventrolateral nucleus of the thalamus or just anterior to the posterior ventral lateral nucleus, are, in addition to Parkinson s disease and Essential cerebellar tremors, dystonia musculorum deformans, hemiballismus, tardive, dyskinesia, and chorea. However, given the fact that deep brain stimulation is drastic surgery, it is often not used with patients who have relatively mild tremor systems.

In this regard, some diseases which produce tremor symptoms are progressive at a relatively rapid rate, e.g., Parkinson's disease, while others are not, e.g., Essential tremors.

Given the fact that medication has proved unsatisfactory as a treatment for tremors and given the further fact that drastic surgery such as deep brain stimulation is not generally used to treat mild tremors, a need for a method and means for effectively treating mild tremors as a stand-alone treatment or as an adjunct to other treatments has long existed, as well as a similar need for effectively treating severe tremors.

The precise pathophysiology of Essential tremor is unknown, but it is believed to involve the cerebellum. The cerebellar outflow to the thalamus appears to be critical, and the cerebellar-thalamic projection site is the frequent target of neurosurgical therapies for intractable Essential tremor. Thus, similarity to the surgical treatment for intractable tremor in Parkinson's disease can be seen.

The peripheral nervous system appears to play a critical role in Essential tremor. Beta-adrenergic receptor blocking medications that do not block the brain have some efficacy against this disorder. Essential tremor patients, like those with focal dystonia, often utilize "sensory tricks" such as touching the chin to suppress tremor, or touching the dorsum of the hand to suppress writing tremor. During the act of writing, it has been observed that tremor worsened if the hand is not permitted to touch the writing surface, such that afferent sensory information about the position of the hand is minimized. Such maneuvers may well enhance musculotendinous afferents to the cerebellum, thereby suppressing tremor.

SUMMARY OF THE INVENTION

The present invention provides a non-invasive method of controlling tremor. While the exact mechanism of the present invention is not known with certainty, it is believed likely that enhancement of muscular and tendon afferent sensory function is involved.

In any event, the present invention involves the application of external pressure to certain areas of the patient's body to control tremor. Preferably, this pressure is applied by using a pressure-applying cuff. It is believed that such pressure activates musculotendonis afferents with the result that tremor is controlled or suppressed, but the present invention is not to be tied to that belief.

The desired locations for placement of the pressure cuff are the wrist, above and or below the elbow, and such other locations as may be found to be effective. When placed on the arm, the location of the cuff will typically be within about 5 inches above or below the elbow. When placed on the wrist, the location of the cuff will typically be within about 3 inches of the base of the hand. The location of the pressure cuff may be dependent upon the location of the tremor which it is desired to control or suppress. More than one cuff may be used simultaneously, e.g., one on the wrist and one above and/or below the elbow.

The desired amount of pressure is, because of patient differences, a wide range of pressure, but an effective tremor suppressing pressure can easily be determined empirically, simply be observing the effect on the patient as pressure is applied and increased to the appropriate level. The duration of pressure application is similarly determined empirically. Tremor suppression in legs can be accomplished in the same manner by applying pressure to the area above the ankle or the area above or below the knee. The location, amount and duration of pressure are determined empirically.

BRIEF DESCRIPTION OF THE DRAWINGS

FIG. 1 is an isometric view of a pressure cuff suitable for use in the present invention.

FIG. 2 shows useful locations for the placement of the cuff of the present invention.

DETAILED DESCRIPTION

A preferred embodiment of the cuff, or brace, of the present invention in shown in FIG. 1. As there illustrated, it can be seen that the flexible cuff, or brace, includes a strip of open pore foam 1 with reinforcing material, such as non-woven fabric, 2 bonded to the outside surface of the foam and a like fabric 3 bonded to the inside surface of the foam to facilitate a complete wrapping about a subject's forearm, wrist or other location. The flexible cuff 1 is also provided with a closure means which, in this embodiment, comprises a Velcro strip 4 and a mechanical loop 5 which is attached to cuff 1.

In use, the flexible cuff is positioned at the desired location and pressure is applied by passing closure strap 4 through mechanical loop 5 and pulling on the strap until the desired degree of pressure has been applied. Because of the variability in magnitude of tremor and the variability in the causes of such tremor, it is not possible to quantify the precise pressure which will be appropriate and effective in any given case. However, the requisite degree and duration of pressure can be determined by the patient simply by adjusting the pressure applied by tightening or loosening the strap until control or suppression of the tremor is achieved.

Referring now to the drawing, there is shown flexible brace employing the principles of the present invention, finding general utility for relieving the tremor symptoms prevalent in Essential and Parkinson's type tremor and affecting the aging population. The brace is formed of a laminated strip which includes a relatively soft, fluid (perspiration) passing material 1 such as an open pore urethane foam, and a fabric 2 (woven or nonwoven) which acts as a perspiration wicking agent.

In accordance with one aspect of the present invention, the inner surface of lamination operates with a reinforced trap 4 to form a complete circumferential contact with the subject's wrist or arm near the elbow. The strap may comprise cloth, or a laminate as of open pore foam and cloth, or similar material. The reinforced strap 4 is preferably somewhat narrower than the backer strip 6 and the mechanical loop 5 so it can freely pass through aperture in loop 5 which is attached to backer strip 6. The strap 4 is fastened to the backer by passing through a slot and being wrapped around to meet on itself and be permanently connected by means of sewing or other bonding technique.

The loop 5 may be completely formed when the member is prepared (e.g., molded) or, alternatively, the requisite loop aperture may be formed by a separately attached bar. To this end, the separately attached bar may be in the form of a rectangle with projection such that its ends pass into retaining apertures formed in the outer member and are permanently joined to member. In any event, the free end of the strap passes through the aperture. Alternatively, the slot may be directly formed into the backer.

The composite flexible cuff, or brace, shown in the drawing is affixed in position by the subject who simply passes his arm through the slack loop formed by the inner laminate strip and strap (assuming t hat the strap end has already passed through the aperture). The subject simply pulls the end of the strap back upon itself until the desired degree of tightness has been achieved.

To lock the flexible brace in place, one part of a mating fastener system is fixed on the outer surface of the laminated strip 2 forming one part of a rapid attachment, quick release system well known to those skilled in the art and sold, for example, under the trademark VELCRO. A mating strip to the element is located on the outer surface of the flexible material.

In use, the composite flexible brace is thus readily applied in the manner above described, and, as shown in FIG. 2, provides a firm, reliable mechanical pressure on the wrist or arm near the elbow, relieving the symptoms of tremor and permitting the function of the hands notwithstanding such condition.

The apparatus shown in FIGS. 1 and 2 is exemplary only. Many other constructions of a cuff or sleeve which apply pressure may be used to apply pressure in selected areas on the extremity or circumferentially.

Patient testing of the method and apparatus of the present invention has resulted in substantial overall suppression of tremor. Some patients benefited more than others and, in individual patients, some extremities benefited more or less than others, e.g., right arms as compared with left arms and vice versa.

Although the preferred embodiment of this invention involves the application of circumferential pressure, it is not necessary to do so. Once again, patient variability plays a role in defining the location in pressure can be effectively applied and specific locations can easily be determined empirically.

The foregoing description of the present invention and certain embodiments thereof is for purposes of illustration only and it is to be understood that the scope of the present invention is defined by the clams appended hereto.

What is claimed is:

1. The method of controlling or suppressing tremors in an extremity of a human being comprising:
   selecting a limb of a human being which is undergoing tremor,
   applying pressure to at least one location on said limb to generate a tremor-suppressing stimulus, and
   suppressing said tremor by maintaining said pressure for a desired tremor-suppressing period of time.

2. The method of claim 1 wherein said tremor is caused by Parkinson's disease.

3. The method of claim 1 wherein said tremor is caused by Essential tremor.

4. The method of claim 1 wherein said pressure is applied to a wrist.

5. The method of claim 1 wherein said pressure is applied to an arm below the elbow.

6. The method of claim 1 wherein said pressure is applied to an arm above the elbow.

7. The method of claim 1 wherein said pressure is applied to a leg above the ankle.

8. The method of claim 1 wherein said pressure is applied to a leg above the knee.

9. The method of claim 1 wherein said pressure is applied below the knee.

* * * * *